United States Patent [19]

Bair

[11] Patent Number: 5,241,107

[45] Date of Patent: Aug. 31, 1993

[54] CARBOCYCLIC DERIVATIVES

[75] Inventor: Kenneth W. Bair, Chapel Hill, N.C.

[73] Assignee: Burroughs Wellcome Co., Research Triangle Park, N.C.

[21] Appl. No.: 798,125

[22] Filed: Nov. 14, 1985

[30] Foreign Application Priority Data

Nov. 15, 1984 [GB] United Kingdom ............... 8428931

[51] Int. Cl.$^5$ ........................................... C07C 67/02
[52] U.S. Cl. .................................................. 560/252
[58] Field of Search ............... 560/252; 514/510, 653, 514/655, 555; 564/387; 260/501.1

[56] References Cited

U.S. PATENT DOCUMENTS

| 4,511,582 | 4/1985 | Bair | 514/654 |
| 4,532,344 | 7/1985 | Bair | 560/252 |
| 4,551,282 | 11/1985 | Bair | 260/501.18 |

FOREIGN PATENT DOCUMENTS

0125702A2  11/1984  European Pat. Off. .

OTHER PUBLICATIONS

Bair, K. W., Chem. Abstracts, vol. 102:220604q, 1985.
Bair, K. W., Chem. Abstracts, vol. 102:203771z, 1985.
Arzneim-Forsch./Drug Res. 32(II), No. 9 (1982), Hrabowska et al., Antitumor Activty of 1-Nitro-9-Aminoacridine Derivatives, pp. 1013-1016.

Primary Examiner—Arthur C. Prescott
Assistant Examiner—V. Garner
Attorney, Agent, or Firm—Donald Brown; Lawrence A. Nielsen

[57] ABSTRACT

The present invention relates to compounds of formula (I)

$$ArCH_2R^1 \qquad (I)$$

or a monomethyl or monoethyl ether thereof (the compound of formula (I) including these ethers may contain no more than 30 carbon atoms in total); ethers, esters, thereof; acid addition salts thereof; wherein Ar is a $C_{15-18}$ fused tetracarbocyclic ring system containing 3 or 4 aromatic rings or a $C_{17-22}$ fused pentacarbocyclic ring system containing 4, or 5 aromatic rings, or a substituted derivative thereof; the ring system Ar should be planar or deviate only slightly from planarity. Thus, the ring system contains a maximum of two non-aromatic carbon atoms which may be in the same ring, in which case they are adjacent, or in different rings;

Ar is not perylene, fluoranthene, chrysene, pyrene, or triphenylene;

$R^1$ contains not more than eight carbon atoms and is a group

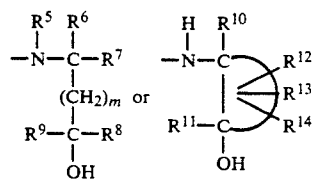

wherein m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

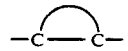

is a five- or six-membered saturated carboxylic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

36 Claims, No Drawings

CARBOCYCLIC DERIVATIVES

The present invention relates to polycyclic alkanol derivatives which have been found to have biocidal activity. More specifically, the invention concerns aminoalkanol derivatives containing a polycarboxylic ring system, methods for the synthesis thereof, novel intermediates therefor, pharmaceutical formulations thereof and the use thereof as biocidal agents, particularly antitumor agents.

Accordingly, in a first aspect, the present invention provides a compound of the formula (I)

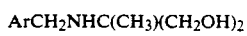    (I)

or a monomethyl or monoethyl ether thereof (the compound of formula (I) including these ethers may contain no more than 30 carbon atoms in total); ethers, esters thereof; acid addition salts thereof; wherein Ar is

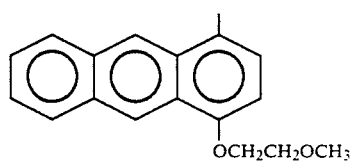

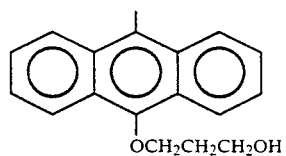

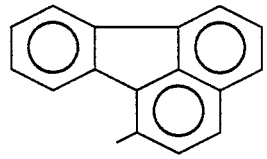

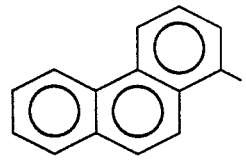

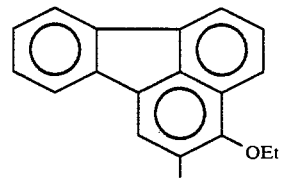

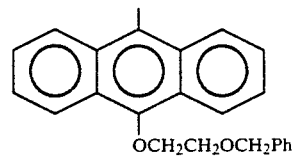

-continued

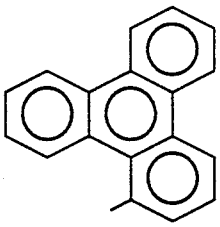

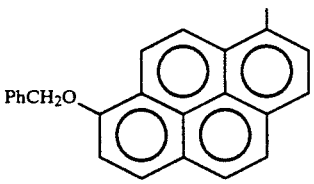

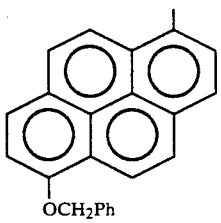

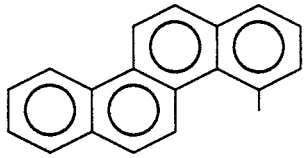

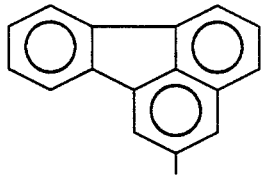

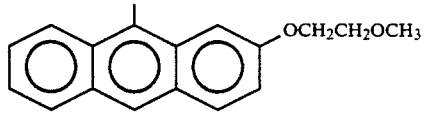

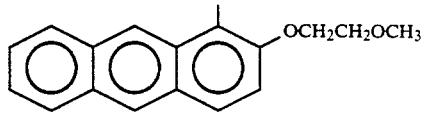

or

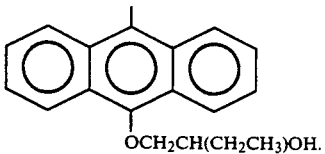

OCH₂CH(CH₂CH₃)OH.

Acid addition salts included within the scope of the present invention are those of compound of formula (I) and ethers and esters thereof.

Esters and nonpharmaceutically useful acid addition salts of the compounds of the formula (I) are useful intermediates in the preparation and purification of compounds of the formula (I) and pharmaceutically useful acid addition salts thereof, and are therefore within the scope of the present invention. Thus, acid addition salts of the compounds of the formula (I) useful in the present invention include but are not limited to those derived from inorganic acids, such as hydrochloric, hydrobromic, sulfuric and phosphoric acids, organic acids such as isethionic (2-hydroxyethylsulfonic), maleic, malonic, salicylic, tartaric, lactic, citric, formic, lactobionic, pantothenic, methanesulfonic, ethanesulfonic, benzenesulfonic, p-toluenesulfonic, naphthalene-2-sulfonic, and ascorbic acids, and amino acids such as glycine.

Acid addition salts particularly useful as biocidal agents are those that are pharmacologically and pharmaceutically acceptable. Thus, suitable acid addition salts include but are not limited to those derived from hydrochloric, methanesulfonic, ethanesulfonic, isethionic, lactic, and citric acids.

The preferred pharmacologically and pharmaceutically acceptable acid addition salts are those that are soluble in solvents suitable for parenteral administration, for example, hydrochlorides, methanesulfonates and isethionates.

Esters of compounds of formula (I) are derived from acids known to those skilled in the art to be suitable for ester formation, and are conveniently those derived from $C_{1-6}$ alkanoic acids or alkanoic acid derivatives, for example acetic acid, propionic acid, n-butyric acid and iso-butyric acid. The esters may be formed from all or only some of the hydroxy groups contained in the compounds of formula (I). Specific compounds within the scope of formula (I) include;

2-[[[4-[2-(Methoxy)ethoxy]-1-anthracenyl]methyl]amino]-2-methyl-1,3-propanediol,
2-[[[10-[3-(Hydroxy)propoxy]-anthracenyl]methyl]amino]-2-methyl-1,3-propanediol,
2-[(1-Fluoranthenylmethyl)amino]-2-methyl-1,3-propanediol,
2-Methyl-2-[(1-phenanthrenylmethyl)amino]-1,3-propanediol,
2-[[(3-Ethoxy-2-fluoranthenyl)methyl]amino]-2-methyl-1,3-propanediol,
2-[[[10-[2-(Benzyloxy)ethoxy]-9-anthracenyl]methyl]amino]-2-methyl-1,3-propanediol,
2-[(1-Triphenylenylmethyl)amino]-2-methyl-1,3-propanediol,
2-[[(8-Benzyloxy-1-pyrenyl)methyl]amino]-2-methyl-1,3-propanediol,
2-[[(6-Benzyloxy-1-pyrenyl)methyl]amino]-2-methyl-1,3-propanediol,
2-[[[10-[2-(Hydroxy)propoxy]-9-anthracenyl]methyl]amino]-2-methyl-1,3-propanediol,
2-[(4-Chrysenylmethyl)amino]-2-methyl-1,3-propanediol,
2-[(2-Fluoranthenylmethyl)amino]-2-methyl-1,3-propanediol,
2-[[[2-[2-(Methoxy)ethoxy]-1-anthracenyl]methyl]amino]-2-methyl-1,3-propanediol,
2-[[[2-[2-(Methoxy)ethoxy]-9-anthracenyl]methyl]amino]-2-methyl-1,3-propanediol and
2-[[[10-[2-(Hydroxy)butoxy]-9-anthracenyl]amino]-2-methyl-1,3-propanediol; ethers, esters thereof; acid addition salts thereof.

Of these specific examples of compounds of formula (I), the preferred compounds are;
2-[[[10-[3-(hydroxy)propoxy]-9-anthracenyl]methyl]amino]-2-methyl-1,3-propanediol,
2-[[[10-[2-(hydroxy)propoxy]-9-anthracenyl]methyl]amino]-2-methyl-1,3-propanediol, and
2-[[[10-[2-(hydroxy)butoxy]-9-anthracenyl]methyl]amino]-2-methyl-1,3-propanediol; ethers, esters thereof; acid addition salts thereof.

The compounds of formula (I) and their ethers, esters and acid addition salts thereof may be prepared by any method known in the art for the preparation of compounds of analogous structure. Thus, the compounds of formula (I) may, for example, be prepared by any of the methods defined below.

1. The reduction of a compound formula (II)

Wherein Ar is as hereinbefore defined or a suitably protected derivative thereof followed by deprotection where appropriate.

The conditions and reagents for such a reaction are well known to those skilled in the art, and any such conditions/reagents may be employed. The conversion of (II) or suitably protected derivatives thereof may be carried out by a reducing agent followed by deprotection if necessary. The reduction is conveniently carried out by a metal hydride such as lithium aluminum hydride, sodium borohydride, sodium cyanoborohydride, or by catalytic hydrogenation, conveniently by hydrogen in the presence of a metal catalyst such as palladium or platinum, or equivalent reagents as outlined by J. March, *Advanced Organic Chemistry*, 2nd ed., pages 819–820, McGraw Hill, New York, 1977. The reduction is suitably carried out with the compound of formula (II) in solution in an inert solvent or mixture of solvents compatible with the reducing agent, at a non-extreme temperature, for example, between 0° and 80° C., conveniently at room temperature.

In the case of lithium aluminum hydride and like reagents, suitable solvents include ethers (for example tetrahydrofuran, diethyl ether and 1,2-dimethoxyethane) optionally in the presence of a hydrocarbon cosolvent (for example toluene, benzene or hexane).

In the case of sodium borohydride and like reagents, suitable solvents include alcohols (for example ethanol, methanol or isopropanol) optionally in the presence of a hydrocarbon cosolvent (for example toluene, benzene or hexane) or an ether cosolvent (for example diethyl ether or tetrahydrofuran).

In the case of sodium cyanoborohydride and like reagents, suitable solvents include those described for sodium borohydride and in the presence of an acid conveniently glacial acetic acid or ethanolic hydrochloric acid as outlined in, for example, R. Hutchins et al., *Organic Preparations and Procedures International* 11, 201 (1979).

In the case of catalytic hydrogenation, suitable solvents include alcohols (for example methanol and ethanol) optionally in the presence of a hydrocarbon cosolvent (for example toluene or benzene) or ether cosolvent (for example diethyl ether or tetrahydrofuran) in the presence of an acid (for example glacial acetic acid or ethanolic hydrochloric acid) or in glacial acetic acid.

Protected derivatives of compounds of formula (II) are conveniently used when lithium aluminum hydride is employed as the reducing agent. Convenient protecting groups are compatible with the reducing agent utilized and are readily removed under nondestructive conditions, for example benzyl, tetrahydropyranyl and isopropylidene ethers.

It is often convenient not to isolate the compound of the formula (II) but to react a compound of the formula (III) with a compound of the formula (IV):

ArCHO                                    (III)

NH$_2$C(CH$_3$)(CH$_2$OH)$_2$            (IV)

wherein Ar and is as defined in (I), and reduce the compound of the formula (II) so formed in situ. The reaction of the compounds of the formulae (III) and (IV) is again suitably carried out using conditions and reagents which are well known to those skilled in the art, for example in the presence of an acid, such as a sulfonic acid, i.e., p-toluenesulfonic acid, in an appropriate inert solvent, such as an aromatic hydrocarbon, suitably toluene, with azeotropic removal of water followed by treatment with the reducing agent in an appropriate solvent, suitably ethanol or methanol. Alternatively, (II) formed under equilibrium conditions in appropriate solvents can be reduced in situ with an appropriate reducing agent, suitably sodium cyanoborohydride. The compound of formula (III) may be in the form of a protected aldehyde, for example an acetal, which liberates the aldehyde function under the reaction conditions.

In turn, a compound of formula (III) can be synthesized by reacting the appropriate polycarbocyclic ring system with a formylating agent such as that generated by the reaction between SnCl$_4$ and Cl$_2$CHOCH$_3$ or equivalent reagents, for example, according to the method of A. Rieche et al., *Chem. Ber.* 93, 88 (1960), or with other standard formylating reagents/procedures known to the art, for example, the Gatterman-Koch reaction (CO/HCl/AlCl$_3$/CuCl), the Gatterman reaction (HCN/HCl/ZnCl$_2$), and the Vilsmeier reaction (POCl$_3$/PhN(Me)CHO, or POCl$_3$/Me$_2$NCHO) (J. March, vide supra, pages 494-497.

The compounds of the formula (III) may also be prepared from an appropriate polycarbocyclic ring system substituted by a suitable functional group such as (but not limited to) esters, CH$_2$OH, CHBr$_2$, CH$_3$, COCH$_3$, COOH, or CN, and converting this functional group to an aldehyde group by methods well known to those skilled in the art.

Where the polycarbocyclic ring system bears substituents, the compound of formula (III) may be prepared by a variety of methods known in the art of organic chemistry depending on the nature of the substituent on the polycyclic ring. For example, if the substituent(s) is a halogen, the starting materials may be prepared by direct treatment of the appropriate polycarbocyclic ring system with a halogenating agent (e.g., Cl$_2$, Br$_2$, or SO$_2$Cl$_2$) or indirectly by such routes as the Sandmeyer reaction (H. H. Hodgson, *Chem. Rev.* 40, 251 (1947). If the substituent(s) is alkyl, the polycarbocyclic ring system may be reacted with the appropriate reagents under Friedel-Crafts reaction conditions (G. A. Olah, *Friedel Crafts and Related Reactions*, Vols. 1-3, Interscience, New York, N.Y., 1963-1965).

2. The reduction of a compound of the formula (V)

wherein Ar is as hereinbefore defined and the hydroxy groups are optionally protected, followed by deprotection of the hydroxy groups where appropriate. The reduction may be carried out by standard reducing agents known for carrying out this type of reduction (as outlined in J. March, vide supra page 1122), for example, a hydride reagent such as lithium aluminum hydride in an inert solvent, such as an ether, i.e., tetrahydrofuran, at a non-extreme temperature, for example, at between 0° and 100° C. and conveniently at the reflux temperature of the ether. The compound of the formula (V) may be formed by the reaction of the appropriate acid (ArCOOH) or a suitable reactive acid derivative thereof (as outlined in J. March, vide supra, pages 382-390), for example, an acid halide, in an inert solvent with an amine of the formula (IV) in which the hydroxy groups are optionally protected, for example, by an isopropylidene group. The compound of the formula (V) so formed is suitably reduced in situ and deprotected if necessary to give a compound of formula (I). The compounds of the formula ArCOOH can be prepared by methods well known to those skilled in the art.

3. The reaction of a compound ArCH$_2$L (wherein Ar is as hereinbefore defined and L is a leaving group) with a compound of the formula (IV) as hereinbefore defined. Suitable leaving groups are those defined by J. March, vide supra, pages 325-331, and include halogens such as chloride and bromine and sulfonic acid derivatives such as p-toluenesulfonate. The reaction is suitably carried out in an appropriate solvent, such as a dipolar aprotic solvent or alcohol at a non-extreme temperature, for example 50°-100°. The compounds of the formula ArCH$_2$L can be prepared by methods well known to those skilled in the art.

There is therefore provided, as a further aspect of the invention, a method for the preparation of a compound of formula (I) comprising any method known for the preparation of analogous compounds, in particular those methods defined in (1) to (3) hereinabove.

The compounds of this invention have biocidal activity, e.g., are toxic to certain living cells which are detrimental to mammals, for example pathogenic organisms and tumor cells. While the compounds herein have biocidal activity, it should be appreciated that the range and level of activity may vary from compound to compound, and therefore the compounds are not necessarily equivalent.

This toxicity to pathogenic organisms has been demonstrated by activity against viruses (e.g., *Herpes sim-*

*plex* 1/vero), fungi (e.g., *Candida albicans*), protozoa (e.g., *Eimeria tenella* and *Trichomonas vaginalis*), bacteria (e.g., *Mycoplasma smegmatis* and *Streptococcus pyrogenes*), and helminths (e.g., *Nippostrongylus brasiliensis*). The antitumor activity of compounds of formula (I) has been demonstrated in a number of recognized screens and primarily by activity against ascitic P388/0 leukemia.

Preferred compounds of the formula (I) are those which have antitumor activity. The activity against ascitic tumors, including P388/0, is evidenced by reduction of tumor cell number in mammals (for example, mice bearing ascitic tumors) and consequent increase in survival duration as compared to an untreated tumor-bearing control group. Antitumor activity is further evidenced by measurable reduction in the size of solid tumors following treatment of mammals with the compounds of this invention compared to the tumors of untreated control tumor-bearing animals. Compounds of formula (I) are active against murine tumors such as lymphocytic leukemia P388/0, lymphocytic leukemia L1210, melanotic melanoma B16, P815 mastocytoma, MDAY/D2 fibrosarcoma, colon 38 adenocarcinoma, M5076 rhabdomyosarcoma and Lewis lung carcinoma.

Activity in one or more of these tumor tests has been reported to be indicative of antitumor activity in man (A. Goldin et al., in *Methods in Cancer Research* ed. V. T. DeVita Jr. and H. Busch, 16 165, Academic Press, N.Y. 1979).

There are sublines of P388/0 which have been made resistant to the following clinically useful agents: cytosine arabinoside, doxorubicin, cyclophosphamide, L-phenylalanine mustard, methotrexate, 5-fluorouracil, actinomycin D, cis-platin and bis-chloroethylnitrosourea. Compounds of this invention show potent activity against these drug-resistant tumors using the procedure for P388/0 above.

Compounds of formula (I) have also been found to be active against human tumor cells in primary cultures of lung, ovary, breast, renal, melanoma, unknown primary, gastric, pancreatic, mesothelioma, myeloma, and colon cancer. As used herein "cancer" is to be taken as synonymous with "malignant tumor" or more generally "tumor" unless otherwise noted. This is a procedure in which the prevention of tumor cell colony formation, i.e., tumor cell replication, by a drug has been shown to correlate with clinical antitumor activity in man (D. D. Von Hoff et al., *Cancer Chemotherapy and Pharmacology* 6, 265 (1980); S. Salmon and D. D. Von Hoff, *Seminars in Oncology*, 8, 377 (1981)).

Compounds of formula I which have been found to have antitumor activity intercalate in vitro with DNA (this property is determined by viscometric methods using the procedure of W. D. Wilson et al., *Nucleic Acids Research* 4, 2697 (1954)) and a log P as calculated by the method of C. Hansch and A. Leo in *Substituent Constants for Correlation Analysis in Chemistry and Biology*, John Wiley and Sons, New York, 1979, lying in the range between −2.0 and +2.5.

As has been described above, the compounds of the present invention are useful for the treatment of animals (including humans) bearing susceptible tumors. The invention thus further provides a method for the treatment of tumors in animals, including mammals, especially humans, which comprises the administration of a clinically useful amount of compound of formula (I) in a pharmaceutically useful form, once or several times a day or other appropriate schedule, orally, rectally, parenterally, or applied topically.

In addition, there is provided as a further, or alternative, aspect of the invention, a compound of formula (I) for use in therapy, for example as an antitumor agent.

The amount of compound of formula (I) required to be effective as a biocidal agent will, of course, vary and is ultimately at the discretion of the medical or veterinary practitioner. The factors to be considered include the condition being treated, the route of administration, the nature of the formulation, the mammal's body weight, surface area, age and general condition, and the particular compound to be administered. A suitable effective antitumor dose is in the range of about 0.1 to about 120 mg/kg body weight, preferably in the range of about 1.5 to 50 mg/kg, for example 10 to 30 mg/kg. The total daily dose may be given as a single dose, multiple doses, e.g., two to six times per day, or by intravenous infusion for a selected duration. For example, for a 75 kg mammal, the dose range would be about 8 to 9000 mg per day, and a typical dose would be about 2000 mg per day. If discrete multiple doses are indicated, treatment might typically be 500 mg of a compound of formula (I) given 4 times per day in a pharmaceutically useful formulation.

While it is possible for the active compound (defined herein as compound of formula (I), or ether, ester, or salt thereof) to be administered alone, it is preferable to present the active compound in a pharmaceutical formulation. Formulations of the present invention, for medical use, comprise an active compound together with one or more pharmaceutically acceptable carriers thereof and optionally other therapeutic ingredients. The carrier(s) must be pharmaceutically acceptable in the sense of being compatible with the other ingredients of the formulation and not deleterious to the recipient thereof.

The present invention, therefore, further provides a pharmaceutical formulation comprising a compound of formula (I) (in the form of the free base, ether, or ester derivative or a pharmaceutically acceptable acid addition salt thereof) together with a pharmaceutically acceptable carrier therefor.

There is also provided a method for the preparation of a pharmaceutical formulation comprising bringing into association a compound of formula (I), an ether, ester, or pharmaceutically acceptable salt thereof, and a pharmaceutically acceptable carrier therefor.

While the antitumor activity of the compounds of formula (I) is believed to reside in the free base, it is often convenient to administer an acid addition salt of a compound of formula (I).

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Molded tablets may be made by molding in a suitable machine, a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredient, such as a polyhydric alcohol for example glycerol or sorbitol. Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter.

Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The following examples are provided by the way of illustration of the present invention and should in no way be construed as a limitation thereof.

General Comments

All solvents were reagent grade and used without further purification with the following exceptions. THF was dried by distillation from Na/K alloy under nitrogen ($N_2$) and used immediately. Toluene ($PhCH_3$) was distilled from $CaH_2$ under $N_2$ and stored over 3Å molecular sieves. Chemicals used were reagent grade and used without purification unless noted. The full name and address of the suppliers of the reagents and chemicals is given when first cited. After this, an abbreviated name is used.

Preparative HPLC was carried out on a Water's Prep LC/System 500A machine using two 500 g silica gel ($SiO_2$) cartridges unless otherwise noted. Plugs of $SiO_2$ used for purifications were "flash chromatography" $SiO_2$ (Merck & Co., Inc., Merck Chemical Division, Rahway, N.J., 07065, Silica Gel 60, 230–400 mesh). In this procedure, an appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flash moved the eluting solvent through the plug rapidly. The appropriate size fractions were combined as needed and further manipulated.

General procedures are described in detail. Analogous procedures show melting point (MP), recrystallization solvents, and elemental analyses (all elements analyzing within a difference of $\leq 0.4\%$ of the expected value). Any changes to the procedure such as solvent, reaction temperature, reaction time, or workup are noted.

NMR ($^1H$, $^{13}C$), IR and MS data of all new products were consistent with the expected and proposed structures. The positions assigned to structural isomers were unequivocally determined by a number of NMR techniques. All final products were dried in a vacuum oven at 20 mm Hg pressure at the temperature indicated overnight (12–16 h). All temperatures are in degrees Celsius. Other abbreviations used are: room temperature (RT), absolute (abs.), round bottom flask (RB flask), minutes (min), hours (h).

EXAMPLE 1

2-[[[4-[2-(Methoxy)ethoxy]-1-anthracenyl]methyl]amino]-2-methyl-1,3-propanediol 1A. 1-[2-(Methoxy)ethosy]anthraquinone To a 5 L 3-necked RB flask equipped with overhead stirrer, thermometer, condenser, and $N_2$ inlet line with bubbler was added 2-methoxyethanol (Mallinckrodt Co., St. Louis, Mo. 63147, 1600 mL, distilled from Na) and KOt-Bu (MCB Manufacturing Chemists, Inc., 2909 Highland Ave., Cincinnati, Ohio 45212, 138.0 g, 1.23 mol). The mixture was stirred for 15 min at RT. To the flask was added 1-chloroanthrquinone (Aldrich Chemical Co., P.O. Box 2060, Milwaukee, Wis. 53201, 194.4 g, 0.80 mol). The reaction mixture was refluxed for 2 h (the mixture became homogeneous as the reaction temperature reached 85°). At this point 800 mL of 2-methoxyethanol was removed from the reaction mixture by distillation. Upon cooling the reaction mixture solidified. The mass was broken-up and diluted to 6 L with $H_2O$ and stirred overnight. The yellow solid was filtered, washed with $H_2O$ (3×500 mL) and dried in a vacuum oven overnight (60°). Recrystallization from EtOAc gave 192.9 g (85.1% yield) of 1-[2-(methoxy)ethoxy]anthraquinone, mp 146°–147°, (C,H).

1B. 1-[2-(Methoxy)ethoxy]anthracene

To a 5 L 3-necked RB flask equipped with overhead stirrer, thermometer, condenser and $N_2$ inlet line with bubbler was added 1-[2-(methoxy)ethoxy]anthraquinone (1A, 90.0 g, 0.319 mol), Zn dust (Mallinckrodt, 200.5 g, 3.19 mol), $CuSO_4$ (Mallinckrodt, 2.2 g), and concentrated $NH_4OH$ (Mallinckrodt, 28%, 2.0 L). The reaction turned a very dark reddish-brown color. The reaction mixture was warmed slowly to reflux over 6 h during which large amounts of $NH_3$ gas were evolved. The reaction mixture was cooled and an additional 500 mL of $NH_4OH$ was added. After warming the reaction mixture was refluxed an additional 5 h. The color of the mixture lightened considerably to a pale yellow color and the unreacted Zn became visible. The reaction mixture was then cooled and filtered. The unreacted Zn was washed with EtOAc (6×500 mL). the filtrate was acidified with con. HCl, and extracted with EtOAc (6×1 L). The EtOAc extracts were combined, dried ($Na_2SO_4$) and concentrated to give a pale yellow solid.

To the flask was added i-PrOH (1.5 L) and after warming to achieve solution the mixture was acidified to pH 4 with con. HCl. After refluxing for 2 h the reaction was neutralized with solid $NaHCO_3$, filtered and the solvent removed by rotary evaporation. The dark oil obtained was dissolved in $PhCH_3$ and chromatographed on a plug of $SiO_2$ using $PhCH_3$ as the eluting solvent. The appropriate fractions were combined and the solvent removed by rotary evaporation to give 60.3 g (75%) of 1-[2-(methoxy)ethoxy]anthracene as an oil which was used without further purification.

1C. 4-[2-(Methoxy)ethoxy]anthracene-1-carbaldehyde

To a 1 L 3-necked RB flask equipped with overhead stirrer, condenser, addition funnel and $N_2$ inlet line with bubbler was added N-methylformanilide (Aldrich, 72 g, 0.53 mol, 65.75 mL) and $CH_2Cl_2$ (150 mL). After cooling to 0°, $POCl_3$ (Aldrich, 69.0 g, 0.44 mol, 42 mL) was added dropwise (maintaining the reaction mixture at 0°) over 20 min. The solution was allowed to warm to RT and a solution of 1-[(2-methoxy)ethoxy]anthracene (1B, 60.0 g, 0.24 mol) in $CH_2Cl_2$ (200 mL) added dropwise over 10 min. The solution warmed and turned a deep red color during this addition. The reaction mixture was refluxed for 5 h, cooled and hydrolyzed by the dropwise addition of $H_2O$ (50 mL) over 1 h. The $H_2O$ was then removed and the volume of the solution reduced to 200 mL. the solution was applied to a plug of $SiO_2$ (1 kg) and chromatographed using $CH_2Cl_2$ followed by EtOAc as the eluting solvents. The appropriate fractions were combined and the solvent removed by rotary evaporation to give a yellow oil which solidified upon cooling. Recrystallization (abs. EtOH) gave 40.87 g (60.7%) of yellow 4-[2-(methoxy)ethoxy]-1-anthracenecarbaldehyde, m.p. 72°–74°, (C,H).

1D. 2-[[[4-[2-(Methoxy)ethoxy]-1-anthracenyl]methyl]amino]-2-methyl-1,3-propanediol hydrochloride To a RB flask equipped with magnetic stirring bar, condenser, Dean-Stark trap and $N_2$ inlet line with bubbler was added 4-[2-(methoxy)ethoxy]-anthracene-1-carbaldehyde (1C, 28.12 g, 0.10 mol), 2-amino-2-methyl-1,3-propanediol (Aldrich, 10.51 g, 0.10 mol), p-toluenesulfonic acid (Aldrich, 100 mg) and $PhCH_3$ (500 mL). The reaction was refluxed with azeotropic removal of $H_2O$ for 3.5 h. Most of the $PhCH_3$ (200 mL) was removed by distillation. The mixture was cooled with an ice bath and diluted with abs. EtOH (200 mL). to the mixture was added solid $NaBH_4$ (Morton-Thiokol, Inc., Alfa Products, P. O. Box 299, 152 Andover St., Danvers, Mass. 01923, 3.78 g, 0.10 mol) in one portion. The reaction was allowed to warm to RT and then stirred overnight. To the reaction mixture was then added 50 mL of 10% HCl solution. The solvents were then removed by rotary evaporation. The solid was transferred to a flask and dissolved in an ethanolic HCl solution, filtered and diluted to 2 L with $Et_2O$. After filtration the solid was recrystallized (EtOH/$Et_2O$) to give after drying 13.19 g (32.5% of 2-[[[4-[2-(methoxy)ethoxy]-1-anthracenyl]methyl]amino]-2-methyl-1,3-propanediol hydrochloride, mp 191°–192°, (C,H,N,Cl).

EXAMPLE 2

2-[[[10-[3-(Hydroxy)propoxy]-9-anthracenyl]methyl]amino]-2-methyl-1,3-propanediol 2A. 10-[3-(Hydroxy)propoxy]anthracene-9-carbaldehyde To a 1 L 3-necked RB flask equipped with overhead stirrer, condenser, thermometer and $N_2$ inlet line with bubbler was added 1,3-propanediol (Aldrich, 500 mL) and KOt-Bu (MCB, 14.03 g, 0.125 mol). After stirring for 30 min 10-chloro-9-anthracenecarbaldehyde (Aldrich, 25.0 g, 0.104 mol) was added to the flask and the mixture further stirred at 90° for 2.5 h. The reaction mixture was poured into $H_2O$ (5 L), filtered, dissolved in EtOAc, washed with $H_2O$ (3×500 mL), dried ($Na_2SO_4$), filtered and the solvent removed to give 24.98 g of dark oil. This was divided into two portions and each purified by preparative HPLC using $SiO_2$ columns and EtOAc/$CH_2Cl_2$ (1:9) as the eluting solvent. Combination of the appropriate fractions followed by removal of the solvents by rotary evaporation gave 19.8 g (66%) of an orange solid, 10-[(3-hydroxy)propoxy]-9-anthracenecarbaldehyde, mp 72°–73°, (C,H).

2B. 2-[[[10-[3-(Hydroxy)propoxy]-9-anthracenyl]methyl]amino]-2-methyl-1,3-propanediol hydrochloride Using the procedure outlined in Example 1D, 10-[3-(hydroxy)propoxy]-9-anthracenecarbaldehye (2A) and 2-amino-2-methyl-1,3-propanediol (Aldrich) gave the crude HCl salt which was purified in the following manner. The material was partitioned between EtOAc and 0.1N NaOH. The basic layer was removed and the EtOAc layer washed with saturated NaCl, dried ($K_2CO_3$) and the solvent removed by rotary evaporation to give the crude free base as a solid. This was dissolved in an ethanolic HCl solution, filtered and the resulting HCl salt precipitated by the addition of $Et_2O$. Filtration and crystallization (i-PrOH/$Et_2O$, 2:3) gave 2-[[[10-[3-(hydroxy)propoxy]-9-anthracenyl]methyl]amino]-2-methyl-1,3-propanediol hydrochloride, mp 175.5°–176.5°, (C,H,N,Cl).

EXAMPLE 3

2-[(1-Fluoranthenylmethyl)amino]-2-methyl-1,3-propanediol

3A. Methyl-1-fluoranthencarboxylate

To a RB flask equipped with magnetic stirrer, condenser and $N_2$ inlet line with bubbler was added methyl, 1,2,3,10b-tetrahydro-1-fluoranthenecarboxylate (Cambridge Chemical, Inc., 202 E. Smith Street, Milwaukee, Wis. 53207, 98.0 g, 0.372 mol), DDQ (Aldrich, 177.0 g, 0.781 mol) and dry $PhCH_3$ (2 L). The reaction mixture was heated at 90° for 10 h, cooled, filtered and concentrated to a 500 mL volume. The crude material was purified on a plug of $SiO_2$ (0.5 kg) using $PhCH_3$ as the eluting solvent. The appropriate fractions were combined and concentrated by rotary evaporation to give a crude pale yellow solid which was recrystallized ($CH_2Cl_2$/hexane), filtered and dried to give 94.5 g (96%) of methyl-1-fluoranthenecarboxylate mp 70°–71°, (C,H).

3B. 1-Hydroxymethylfluoranthene

To a RB flask equipped with magnetic stirrer, condenser, and $N_2$ inlet line with bubbler was added methyl-1-fluoranthenecarboxylate (3A, 71.54 g, 0.275 mol), $LiBH_4$ (Aldrich, 100 g, 0.459 mol) and dry THF (1 L). The mixture was refluxed overnight, cooled and poured into $H_2O$ (2 L). The mixture was cautiously acidified with 1N HCl, filtered and the resulting solid washed with H₂O (2×300 mL). After recrystallization (CH₂Cl₂/hexane) and drying, 54.75 g (86%) of 1-hydroxymethylfluoranthene was obtained, mp 147°-185°, (C,H).

3C. 1-Chloromethylfluoranthene

To a RB flask equipped with magnetic stirring bar, condenser, addition funnel, thermometer and N₂ inlet line with bubbler was added 1-hydroxymethylfluoranthene (3B, 12.0 g, 0.052 mol), and dry PhCH₃ (500 mL). To the mixture was added SOCl₂ (Aldrich, 15.73 g, 0.132 mol, 9.5 mL) dropwise over 15 min. The mixture was then heated at 80° overnight and then refluxed for 1 h. The solvent was removed by rotary evaporation to give a crude off white solid. The material was redissolved in PhCH₃ (300 mL) followed again by rotary evaporation. The process was repeated two additional times to give the crude product 1-chloromethylfluoranthene which was used without further purification.

3D. 2-[(1-Fluoranthenylmethyl)amino]-2-methyl-1,3-propanediol hydrochloride 0.3 H₂O To a RB flask equipped with magnetic stirring bar, condenser and N₂ inlet line with bubbler was added crude 1-chloromethylfluoranthene (3C, 13.01 g, 52 mmol), 2-amino-2-methyl-1,3-propanediol (Aldrich, 5.46 g, 52 mmol), K₂CO₃ (MCB, 14.37 g, 0.104 mol) and abs. EtOH (300 mL). The reaction was stirred at reflux overnight, filtered hot, and the solvent removed by rotary evaporation to give a crude dark oil. This was acidified with 1N HCl and dissolved in H₂O, filtered, basified with 5N NaOH solution and filtered to give a crude white solide. The material was dissolved in ethanolic HCl solution, filtered and precipitated with Et₂O. Filtration followed by crystallization (abs. EtOH/Et₂O, 1:4) gave after filtration and drying a 43.8% yield of 2-[(1-fluorantheneylmethyl)amino]-2-methyl-1,3-propanediol hydrochloride 0.3 H₂O, mp 185-188 (dec), (C,H,N,Cl).

EXAMPLE 4

2-Methyl-2-[(1-phenanthrenylmethyl)amino]-1,3-propanediol 4A. 1-Bromomethylphenanthrene To a RB flask equipped with stirring bar, N₂ inlet line with bubbler was added 1-methylphenanthrene (Cambridge Chemical, Inc., 25.0 g, 0.130 mol), N-bromosuccinimide (Aldrich (recrystallized from H₂O and dried overnight under high vacuum), 25.45 g, 0.143 mol), benzoyl peroxide (Aldrich, 100 mg) and CCl₄ (500 mL). The mixture was stirred at reflux for 2.5 h, cooled and the succinimide formed in the reaction removed by filtration. The solvent was removed from the filtrate by rotary evaporation and the residue dissolved in EtOAc (650 mL), washed with H₂O (3×150 mL) and dried (Na₂SO₄). The solvent was then removed by rotary evaporation and the crude product recrystallized (hexane/EtOAc, 10:1), filtered and dried to give 25.3 g (72.8% yield) of 1-bromophenanthrene, mp 90°-91°, (C,H,Br).

4B. 2-Methyl-2-[(1-phenanthrenylmethyl)amino]-1,3-propanediol hydrochloride

Using the procedure outlined in Example 3D, 1-bromophenanthrene (4A) and 2-amino-2-methyl-1,3-propanediol (Aldrich) gave a 23.9% yield of 2-methyl-2-[(1-phenanthrenylmethyl)amino]-1,3-propanediol hydrochloride, mp 210°-211°, (C,H,N,Cl), (EtOH/Et₂O).

EXAMPLE 5

2-[[(3-Ethoxy-2-fluoranthenyl)methyl]amino]-2-methyl-1,3-propanediol 5A. 3-Ethoxyfluoranthene-2-carbaldehyde 3-Ethoxyfluoranthene (Cambridge Chemical, Inc.) was formylated using the procedure of A. Rieche et al., Chem. Ber. 93, 88 (1960) to give a 65.3% yield of 3-ethoxyfluoranthene-2-carbaldehyde, mp 164°-166°, (C,H), (CH₂Cl₂/hexane), along with a small amount (1%) of 4-ethoxyfluoranthene-8-carbaldehyde, mp 117.5°-119°, (C,H), (CH₂Cl₂/hexane.

5B. 2-[[(3-Ethoxy-2-fluoranthenyl)methyl]amino]-2-methyl-1,3-propanediol methanesulfonate.0.25 EtOH Using the procedure outlined in Example 1D, 3-ethoxyfluoranthene-2-carbaldehyde (5B) and 2-amino-2-methyl-1,3-propanediol (Aldrich) gave a 80.7% yield of 2-[[(3-ethoxy-2-fluoranthenyl)methyl]amino]-2-methyl-1,3-propanediol methanesulfonate.0.25 EtOH, mp 190°-192° (dec), (C,H,N,S), (EtOH/Et₂O).

EXAMPLE 6

2-[[[10-[2-(Benzyloxy)ethoxy)-9-anthracenyl]methyl]amino]-2-methyl-1,3-propanediol 6A. 10-[2-Benzyloxy)ethoxy]anthracene-9-carbaldehyde Using the procedure outlined in Example 2A, 10-chloroanthracene-9-carbaldehyde (Aldrich) and 2-benzyloxyethanol (Aldrich) gave a 29.5% yield of 10-[2-(benzyloxy)ethoxy]anthracene-9-carbaldehyde, mp 68°-69°, (C,H), (CH₂Cl₂/hexane).

6B. 2-[[[10-[2-(Benzyloxy)ethoxyl]-9-anthracenyl]methyl]amino]-2-methyl-1,3-propanediol hydrochloride Using the procedure outlined in Example 1D, 10-[2-(benzyloxy)ethoxy]anthracene-9-carbaldehye (6A) and 2-amino-2-methyl-1,3-propanediol (Aldrich) gave a 47.4% yield of 2-[[[10-[2-(benzyloxy)ethoxy]-9-anthracenyl]methyl]amino]-2-methyl-1,3-propanediol hydrochloride, mp 172.5°-174° (dec), (C,H,N,Cl), (EtOH/Et₂O).

EXAMPLE 7

2-[(1-Triphenylenylmethyl)amino]-2-methyl-1,3-propanediol 7A. 1-Bromomethyltriphenylene Using the procedure outlined in Example 4A, 1-methyltriphenylene (Cambridge Chemical, Inc.) gave a near quantitative yield of crude 1-bromomethyltriphenylene which was used without further purification.

7B. 2-[(1-Triphenylenylmethyl)amino]-2-methyl-1,3-propanediol hydrochloride

Using the procedure outlined in Example 3D, 1-bromomethyltriphenylene (7A) and 2-amino-2-methyl-1,3-propanediol (Aldrich) gave an 11.3% yield of 2-[(1-triphenylenylmethyl)amino]-2-methyl-1,3-propanediol hydrochloride. mp 200°-203°, (C,H,N,Cl), (EtOH-/Et₂O).

EXAMPLE 8

2-[[(8-Benzyloxy-1-pyrenyl)methyl]amino]-2-methyl-1,3-propanediol and

2-[[(6-Benzyloxy-1-pyrenyl)methyl]amino]-2-methyl-1,3-propanediol 8A. 1-Benzyloxyprene To a RB flask equipped with overhead stirrer, condenser and N₂ inlet line with bubbler was added 1- hydroxypyrene (Cambridge Chemical, Inc., 5.0 g, 23 mmol), benzyl bromide (Aldrich, 15.64 g, 92 mmol, 10.94 mL), K$_2$CO$_3$ (Mallinckrodt, 12.72 g, 92 mmol) and acetone (100 mL). The mixture was refluxed overnight, cooled and then poured into H$_2$O (250 mL) and extracted with EtOAc (3×100 mL). The EtOAc layers were combined and washed successively with 1N NaOH (100 mL), H$_2$O (100 mL) and saturated NaCl solution (2×100 mL). The solution was then dried (K$_2$CO$_3$) and the solvent removed by rotary evaporation to give the crude product. This material was purified by passing it through a plug of SiO$_2$ using PhCH$_3$ as the eluting solvent. The solvent was then removed from the appropriate fractions by rotary evaporation and the solid recrystallized from CH$_2$Cl$_2$/hexane to give 1.78 g (25.9% yield) of 1-benzyloxypyrene, mp 105°–106°, (C,H).

8B. 6- and 8-Benzyloxypyrene-1-carbaldehydes

1-Benzyloxyprene was formylated using the method of A. Rieche et al., Chem. Ber. 93, 88 (1960) to give a 1:1 ratio of 6- and 8-benzyloxypyrene-1-carbaldehydes in 43% yield which could not be separated by fractional crystallization or chromatography. The mixture was used without further purification.

8C. 2-[[(8-Benzyloxy-1-pyrenyl)methyl]amino]-2-methyl-1,3-propanediol hydrochloride 8D. 2-[[(6-Benzyloxy-1-pyrenyl)methyl]amino]-2-methyl-1,3-propanediol hydrochloride Using the procedure outlined in Example 1D, the mixture of 6- and 8-benzyloxyprene-1-carbaldehydes (8A and 8B) and 2-amino-2-methyl-1,3-propanediol (Aldrich) gave a 1:1 crude mixture of 2-[[(8-benzyloxy-1-pyrenyl)methyl]amino]-2-methyl-1,3-propanediol hydrochloride and 2-[[(6-benzyloxy-1-pyrenyl)methyl]amino]-2-methyl-1,3-propanediol hydrochloride. The crude mixture (two spots by TLC) was purified by fractional crystallization in the following manner: the crude solid was treated three times with boiling abs. EtOH. The middle fraction still contained a mixture of the two components and was discarded. The first and third fractions were diluted with Et$_2$O and the resultant solids filtered. The first fraction was crystallized three times from i-PrOH/Et$_2$O to give 16.6% yield of 2-[[(8-benzyloxy-1-pyrenyl)methyl]amino]-2-methyl-1,3-propanediol hydrochloride, mp 186°–192°, (C,H,N,Cl) and the third fraction crystallized three times from EtOH/Et$_2$O to give 2-[[(6-benzyloxy-1-pyrenyl)methyl]amino]-2-methyl-1,3-propanediol hydrochloride, mp 227°–229°, (C,H,N,Cl).

EXAMPLE 9

2-[[[10-[2-(Hydroxy)propoxy]-9-anthracenyl]methyl]amino]-2-methyl-1,3-propanediol 9A. 10-[2-(Hydroxy)propoxy]anthracene-9-carbaldehyde Using the procedure outlined in Example 2A, 10-chloroanthracene-9-carbaldehyde (Aldrich) and 1,2-propyleneglycol (Aldrich) gave a 29.5% yield of 10-[2-(hydroxy)propoxy]anthracene-9-carbaldehyde, mp 84°–86°, (C,H), (pentane).

9B. 2-[[[10-[2-(Hydroxy)propoxy]-9-anthracenyl]methyl]amino]-2-methyl-1,3-propanediol hydrochloride Using the procedure outlined in Example 1D, 10-[2-(hydroxy)propoxy]-anthracene-9-carbaldehyde (9A) and 2-amino-2-methyl-1,3-propanediol (Aldrich) gave a 22.1% yield of 2-[[[10-[2-(hydroxy)propoxy]-9-anthracenyl]methyl]amino]-2-methyl-1,3-propanediol hydrochloride, mp 171°–174° (dec), (C,H,N,Cl), (i-PrOH/Et$_2$O).

EXAMPLE 10

2-[(4-Chrysenylmethyl)amino]-2-methyl-1,3-propanediol 10A. 4-Bromomethylchrysene Using the procedure outlined in Example 4A, 4-methylchrysne (Cambridge Chemical, Inc.) gave a nearly quantitative yield of crude 4-bromomethylchrysene which used without further purification.

10B. 2-[(4-Chrysenylmethyl)amino]-2-methyl-1,3-propanediol methanesulfonate 0.4 H$_2$O 0.1 i-PrOH Using the procedure outlined in Example 3D except that the crude free base was treated with methanesulfonic acid, 4-bromomethylchrysene (10A) and 2-amino-2-methyl-1,3-propanediol (Aldrich) gave a 27.5% yield of 2-[(4-chrysenylmethyl)amino]-2-methyl-1,3-propanediol methanesulfonate 0.4 H$_2$O 0.1 i-PrOH, mp 192°–193.5° (C,H,N,S), (i-PrOH/Et$_2$O).

EXAMPLE 11

2-[(2-Fluoranthenylmethyl)amino]-2-methyl-1,3-propanediol 11A. 2-Bromomethylfuranethene Using the procedure outlined in Example 4A, 2-methylfluoranthene (Cambridge Chemical, Inc.) gave a 92% yield of crude 2-bromomethylfluoranthene which was used without further purification.

11B. 2-[(2-Fluoranthenylmethyl)amino-2-methyl-1,3-propanediol hydrochloride 0.2 H$_2$O Using the procedure outlined in Example 3D, 2-bromomethylfluoranthene (10A) and 2-amino-2-methyl-1,3-propanediol (Aldrich) gave a 15.7% yield of 2-[(2-fluoranthenylmethyl)amino]-2-methyl-1,3-propanediol hydrochloride 0.2 H$_2$O, mp 193°–194°, (C,H,N,Cl), (i-PrOH/Et$_2$O).

EXAMPLE 12

2-[[[2-[2-(Methoxy)ethoxy]-1-anthracenyl]methyl]amino]-2-methyl-1,3-propanediol 12A. 2-[2-(Methoxy)ethoxy]anthraquinone Using the procedure outlined in Examples 1A, 2-chloroanthraquinone (Aldrich) and methoxyethanol (Aldrich) gave a 44.3% yield of 2-[2-(methoxy)ethoxy)]anthraquinone, mp 126°, (C,H), (CH$_2$Cl$_2$/hexane).

12B. 2-[2-(Methoxy)ethoxy]anthracene

Using the procedure outlined in Example 1B, 2-[2-(methoxy)ethoxy]anthraquinone (12A) gave a 50.6% yield of 2-[2-(methoxy)ethoxy]anthracene, mp 131°–134°, (C,H), (CH$_2$Cl$_2$/hexane).

12C. 2-[2-(Methoxy)ethoxy]anthracene-1-carbaldehyde 12D. 2-[2-(Methoxy)ethoxy]anthracene-9-carbaldehyde Using the procedure outlined in Example 1C, 2-[2-(methoxy)ethoxy]anthracene (12B) gave after crystallization (abs. EtOH) a 2:1 mixture of two aldehydes in 86% overall yield. The isomers were separated by column chromatography on SiO$_2$ using EtOAc/hexane (1:1) as the eluting solvent. After crystallization (PhCH$_3$/hexane) a 34.4% yield of the more mobile aldehyde was obtained which was identified as 2-[2-(methoxy)ethoxy]anthrancene-9-carbaldehyde, mp 85.5°–87.5°, (C,H). The less mobile isomer was crystallized from PhCH$_3$ to give a 13.5% yield of 2-[2-(methoxy)ethoxy]anthracene-1-carbaldehyde, mp 114.5°–117°, (C,H).

12E. 2-[[[2-[2-(Methoxy)ethoxy]-1-anthracenyl]methyl]amino]-2-methyl-1,3-propanediol hydrochloride Using the procedure outlined in Example 1D, 2-[2-(methoxy)ethoxy]anthracene-1-carbaldehyde (12C) and 2-amino-2-methyl-1,3-propanediol (Aldrich) gave a 52.8% yield of 2-[[[2-[2-(methoxy)ethoxy]-1-anthracenyl]methyl]amino]-2-methyl-1,3-propanediol hydrochloride, mp 178°–179.5° (dec), (C,H,N,Cl), (EtOH/Et$_2$O).

EXAMPLE 13

2-[[[2-[2-(Methoxy)ethoxy]-9-anthracenyl]methyl]amino]-2-methyl-1,3-propanediol hydrochloride Using the procedure outlined in Example 1D, 2-[2-(methoxy)ethoxy]anthracene-9-carbaldehyde (12D) and 2-amino-2-methyl-1,3-propanediol (Aldrich) gave a 76.1% yield of 2-[[[2-[2-(methoxy)ethoxy]-9-anthracenyl]methyl]amino]-2-methyl-1,3-propanediol hydrochloride, mp 183°–185.5° (dec), (C,H,N,Cl), (EtOH/Et$_2$O).

EXAMPLE 14

2-[[[10-[2-(Hydroxy)butoxy]-9-anthracenyl]methyl]amino]-2-methyl-1,3-propanediol 14A. 10-[2-(Hydroxy)butoxy]anthracene-9-carbaldehyde Using the procedure outlined in Example 2A except that DMSO was used as the solvent and the reaction run at room temperature, 10-chloroanthracene-9-carbaldehyde and 1,2-butanediol (Aldrich) gave a 50.3% yield of 10-[2-(hydroxy)butoxy]anthracene-9-carbaldehyde, mp 82°–88°, (C,H), (CH$_2$Cl$_2$/petroleum ether).

14B. 2-[[[10-[2-(Hydroxy)butoxy]-9-anthracenyl]methyl]amino]-2-methyl-1,3-propanediol hydrochloride Using the procedure outlined in Example 1D, 10-[2-(hydroxy)butoxy]anthracene-9-carbaldehyde (14A) and 2-amino-2-methyl-1,3-propanediol (Aldrich) gave a 46.8% yield of 2-[[[10-[2-(hydroxy)butoxyl]-9-anthracenyl]methyl]amino]-2-methyl-1,3-propanediol hydrochloride, mp 177°–180° (dec), (C,H,N,Cl), (i-PrOH/Et$_2$O).

Antitumor Screening Results

Methods for evaluating the antitumor activity of these compounds are essentially those used in the Tumor Panel by the Development Therapeutics Program, Division of Cancer Treatment, National Cancer Institute, A. Goldin, et al., *Methods in Cancer Research*, vol XVI, p. 165, Academic Press (1979). Some modifications, in dose level and schedule have been made to increase the testing efficiency.

EXAMPLE 15

Lymphocytic Leukemia P388/0 Test

CD2-F$_1$ mice, of the same sex, weighing 20±3 g, are used for this test. Control and test animals are injected intraperitoneally with a suspension of ~10$^6$ viable P388/0 tumor cells on day 0. In each test, several dose levels which bracket the LD$_{20}$ of the compound are evaluated; each dose level group contains six animals. The test compounds are prepared either in physiologic saline containing 0.05% Tween 80 or distilled water containing 5% dextrose and are administered intraperitoneally on days 1, 5, and 9 relative to tumor implant. Doses are on a mg/kg basis according to individual animals' body weights. The day of death for each animal is recorded, the median identified for each group and the ratios of median survival time for treated (T)/control (C) groups are calculated. The criterion for activity is T/C×100≧120%. Results of P338/0 testing are summarized in Table I below.

TABLE I

| Compound of Formula | Optimal Dose (mg/kg) | T/C × 100% (Excluding 30 Day Survivors) | 30 Day Survivors | LD$_{20}$ (mg/kg) |
|---|---|---|---|---|
| 1D | 170 | +250 | 2/6 | 125 |
| 2B | 125 | +250 | 1/6 | 55 |
| 3C | 140 | +200 | 0/6 | 80 |
| 4B | 260 | +165 | 0/6 | 230 |
| 6B | 150 | +135 | 0/6 | 100 |
| 7B | 165 | +125 | 0/6 | 250 |
| 8C | 200 | +121 | 0/6 | 250 |
| 9B | 110 | +285 | 2/6 | 70 |
| 10B | 225 | +225 | 0/6 | 150 |
| 11B | 160 | +200 | 0/6 | 120 |
| 12E | 45 | +130 | 0/6 | 45 |
| 14B | 150 | +227 | 1/6 | 150 |

EXAMPLE 16

Formulation Examples

| A. TABLET | |
|---|---|
| Compound of Formula I | 500.0 mg |
| Pregelatinized Corn Starch | 60.0 mg |
| Sodium Starch Glycolate | 36.0 mg |
| Magnesium Stearate | 4.0 mg |

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximately 600 mg each.

| B. TABLET | |
|---|---|
| Compound of formula (I) | 500.0 mg |
| Corn Starch | 70.0 mg |
| Lactose | 83.8 mg |
| Magnesium Stearate | 4.2 mg |
| Polyvinylpyrrolidone | 14.0 mg |
| Stearic Acid | 28.0 mg |

The compound of formula (I) is finely ground and intimately mixed with the powdered excipients, corn starch and lactose. The powders are wetted with a solution of polyvinylpyrrolidone dissolved in a mixture of purified water and denatured alcohol to form granules. The granules are dried and mixed with the powdered stearic acid and magnesium stearate. The formulation is then compressed into tablets weighing approximately 700 mg each.

| C. CAPSULES | |
|---|---|
| Compound of formula (I) | 500.0 mg |
| Corn Starch | 50.0 mg |
| Magnesium Stearate | 3.0 mg |

The finely divided compound of formula (I) is mixed with powdered corn starch and wetted with denatured alcohol to densify the powder. The dried powder is mixed with stearic acid and filled into hard-shell gelatin capsules.

| D. SYRUP | |
|---|---|
| Compound of formula (I) | 250.0 mg |
| Ethanol | 250.0 mg |
| Glycerin | 500.0 mg |
| Sucrose | 3,500.0 mg |
| Flavoring Agent | q.s. |
| Coloring Agent | q.s. |
| Preserving Agent | 0.1% |
| Purified Water q.s. to | 5.0 mL |

The compound of formula (I) is dissolved in the ethanol, glycerin, and a portion of the purified water. The sucrose and preserving agent are dissolved in another portion of hot purified water, and then the coloring agent is added and dissolved. The two solutions are mixed and cooled before the flavoring agent is added. Purified water is added to final volume. The resulting syrup is thoroughly mixed.

| E. IV INJECTION | |
|---|---|
| Compound of formula (I) | 5.0 mg |
| Glycerin | q.s. for isotonicity |
| Preservative | 0.1% |
| Hydrochloric Acid or Sodium Hydroxide | as needed for pH adjustment |
| Water for Injection | q.s. to 1 mL |

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled into sterile 10 mL ampules or vials.

What is claimed is:

1. 2-[[[4-2-(Methoxy)ethoxy]-1-anthracenyl]methyl]amino]-2-methyl-1, 3- propanediol or a pharmaceutically acceptable acid addition salt thereof.
2. A compound of claim 1 as an acid addition salt of methanesulfonic, ehtanesulfonic, lactic, citric or isethionic acid.
3. 2-[[[4-[2-(Methoxy)ethoxy]-1-anthracenyl]methyl]amino]-2-methyl-1, 3-propanediol hydrochloride.
4. 2-[[[10-[3-(Hydroxy)propoxy]-9-anthracenyl]methyl]amino]-2-methyl-1,3-propanediol or a pharmaceutically acceptable acid addition salt thereof.
5. A compound of claim 4 as an acid addition salt of methanesulfonic ethanesulfonic, lactic, citric or isethionic acid.
6. 2-[[[10-[3-(Hydroxy)propoxy]-9-anthracenyl]methyl]amino]-2-methyl-1,3-propanediol hydrochloride.
7. 2-Methyl-2-[(1-phenanthrenylmethyl)amino]-1,3-propanediol or a pharmaceutically acceptable acid addition salt thereof.
8. A compound of claim 7 as an acid addition salt of methanesulfonic, ethanesulfonic, lactic, citric or isethionic acid.
9. 2-[[(3-Ethoxy-2-fluoranthenyl)methyl]amino]-2-methyl-1,3-propanediol methanesulfonate.
10. 2-[[[10-[2-(Benzyloxy)ethoxy]-9-anthracenyl]methyl]amino]-2-methyl-1,3-propanediol or a pharmaceutically acceptable acid addition salt thereof.
11. A compound of claim 10 as an acid addition salt of methanesulfonic, ethanesulfonic, lactic, citric or isethionic acid.
12. 2-[[[10-[2-(Benzyloxy)ethoxy]-9-anthracenyl]methyl]amino]-2-methyl-1,3-propanediol hydrochloride.
13. 2-[[(8-Benzyloxy-1-pyrenyl)methyl]amino]-2-methyl-1,3-propanediol or a pharmaceutically acceptable acid addition salt thereof.
14. A compound of claim 13 as an acid addition salt of methanesulfonic, ethanesulfonic, lactic, citric or isethionic acid.
15. 2-[[(8-Benzyloxy-1-pyrenyl)methyl]amino]-2-methyl-1,3-propanediol hydrochloride.
16. 2-[[(6-Benzyloxy-1-pyrenyl)methyl]amino]-2-methyl-1,3-propanediol or a pharmaceutically acceptable acid addition salt thereof.
17. A compound of claim 16 as an acid addition salt of methanesulfonic, ethanesulfonic, lactic, citric or isethionic acid.
18. 2-[[(6-Benzyloxy-1-pyrenyl)methyl]amino]-2-methyl-1,3-propanediol hydrochloride.
19. 2-[[[10-[2-(Hydroxy)propoxy]-9-anthracenyl]-methyl]amino]-2-methyl-1,3-propanediol or a pharmaceutically acceptable acid addition salt thereof.
20. A compound of claim 19 as an acid addition salt of methanesulfonic, ethanesulfonic, lactic, citric or isethionic acid.
21. 2-[[[10-[2-(Hydroxy)propoxy]-9-anthracenyl]methyl]amino]-2-methyl-1,3-propanediol hydrochloride.
22. 2-[(4-Chrysenylmethyl)amino]-2-methyl-1,3-propanediol or a pharmaceutically acceptable acid addition salt thereof.
23. A compound of claim 22 as an acid addition salt of hydrochloric, ethanesulfonic, lactic, citric or isethionic acid.
24. 2-[(4-Chrysenylmethyl)amino]-2-methyl-1,3-propanediol methanesulfonate.
25. 2-[[[2-[2-(Methoxy)ethoxy]-1-anthracenyl]methyl]amino]-2-methyl-1,3-propanediol or a pharmaceutically acceptable acid addition salt thereof.
26. A compound of claim 25 as an acid addition salt of methanesulfonic, ethanesulfonic, lactic, citric or isethionic acid.
27. 2-[[[2-[2-(Methoxy)ethoxy]-1-anthracenyl]methyl]amino]-2-methyl-1,3-propanediol hydrochloride.
28. 2[[[2-[2-(Methoxy)ethoxy]-9-anthracenyl]methyl]amino]-2-methyl-1,3-propanediol or a pharmaceutically acceptable acid addition salt thereof.
29. A compound of 28 as an acid addition salt of methanesulfonic, ethanesulfonic, lactic, citric or isethionic acid.
30. 2-[[[2-[2-(Methoxy)ethoxy]-9-anthracenyl]methyl]amino]-2-methyl-1,3-propanediol hydrochloride.
31. 2-[[[10-[2-(Hydroxy)butoxy]-9-anthracenyl]methyl]amino]-2-methyl-1,3-propanediol or a pharmaceutically acceptable acid addition salt thereof.
32. A compound of claim 31 as an acid addition salt of methanesulfonic, ethanesulfonic, lactic, citric or isethionic acid.
33. 2-[[[10-[2-(Hydroxy)butoxy]-9-anthracenyl]methyl]amino]-2-methyl-1,3-propanediol hydrochloride.
34. A compound of formula (I) is selected from
2-[[[4-[2-(Methoxy)ethoxy]-1-anthracenyl]methyl]amino]-2-methyl-1,3-propanediol hydrochloride,
2-[[[10-[3-(Hydroxy)propoxy]-9-anthracenyl]methyl]amino]-2-methyl-1,3-propanediol hydrochloride,
2-[(1-Fluoranthenylmethyl)amino]-2-methyl-1,3-propanediol hydrochloride, 2-Methyl-2-[(1-phenanthrenylmethyl)amino]-1,3-propanediol hydrochloride,
2-[[(3-Ethoxy-2-fluoranthenyl)methyl]amino]-2-methyl-1,3-propanediol methanesulfonate,
2-[[[10-[2-(Benzyloxy)ethoxy]-9-anthracenyl]methyl-]amino]-2-methyl-1,3-propanediol hydrochloride,
2-[(1-Triphenylenylmethyl)amino]-2-methyl-1,3-propanediol,
2-[[(8-Benzyloxy-1-pyrenyl)methyl]amino]-2-methyl-1,3-propanediol hydrochloride,
2-[[(6-Benzyloxy-1-pyrenyl)methyl]amino]-2-methyl-1,3-propanediol hydrochloride,
2-[[[10-[2-(Hydroxy)propoxy]-9-anthracenyl]methyl-]amino]-2-methyl-1,3-propanediol hydrochloride,
2-[(4-Chrysenylmethyl)amino]-2-methyl-1,3-propanediol methanesulfonate,
2-[(2-Fluoranthenylmethyl)amino]-2-methyl-1,3-propanediol hydrochloride,
2-[[[2-[2-(Methoxy)ethoxy]-1-anthracenyl]methyl-]amino]-2-methyl-1,3-propanediol hydrochloride,
2-[[[2-[2-(Methoxy)ethoxy]-9-anthracenyl]methyl-]amino]-2-methyl-1,3-propanediol hydrochloride or
2-[[[10-[2-(Hydroxy)butoxy]-9-anthracenyl]methyl-]amino]-2-methyl-1,3-propanediol hydrochloride.

35. A compound selected from the group consisting of:

2-[[[4-[2-(Methoxy)ethoxy]-1-anthracenyl]methyl-]amino]-2-methyl-1,3-propanediol,
2-[[[10-[3-(Hydroxy)propoxy]-9-anthracenyl]methyl-]amino]-2-methyl-1,3-propanediol,
2-[(1-Fluoranthenylmethyl)amino]-2-methyl-1,3-propanediol,
2-Methyl-2-[(1-phenanthrenylmethyl)amino]-1,3-propanediol,
2-[[(3-Ethoxy-2-fluoranthenyl)methyl]amino]-2-methyl-1,3-propanediol,
2-[[[10-[2-(Benzyloxy)ethoxy]-9-anthracenyl]methyl-]amino]-2-methyl-1,3-propanediol,
2-[(1-Triphenylenylmethyl)amino]-2-methyl-1,3-propanediol,
2-[[(8-Benzyloxy-1-pyrenyl)methyl]amino]-2-methyl-1,3-propanediol,
2-[[(6-Benzyloxy-1-pyrenyl)methyl]amino]-2-methyl-1,3-propanediol,
2-[[[10-[2-(Hydroxy)propoxy]-9-anthracenyl]methyl-]amino]-2-methyl-1,3-propanediol,
2-[(4-Chrysenylmethyl)amino]-2-methyl-1,3-propanediol,
2-[(2-Fluoranthenylmethyl)amino]-2-methyl-1,3-propanediol,
2-[[[2-[2-(Methoxy)ethoxy]-1-anthracenyl]methyl-]amino]-2-methyl-1,3-propanediol,
2-[[[2-[2-(Methoxy)ethoxy]-9-anthracenyl]methyl-]amino]-2-methyl-1,3-propanediol and
2-[[[10-[2-(Hydroxy)butoxy]-9-anthracenyl]methyl-]amino]-2-methyl-1,3-propanediol or a pharmaceutically acceptable acid addition salt thereof.

36. A compound selected from the group consisting of:

2-[[[10-[3-(hydroxy)propoxy]-9-anthracenyl]methyl-]amino]-2-methyl-1,3-propanediol,
2-[[[10-[2-(hydroxy)propoxy]-9-anthracenyl]methyl-]amino]-2-methyl-1,3-propanediol, and
2-[[[10-[2-(hydroxy)butoxy]-9-anthracenyl]methyl-]amino]-2-methyl-1,3-propanediol or a pharmaceutically acceptable acid addition salt thereof.

* * * * *